US00PP18378P2

(12) United States Plant Patent
Anatriello

(10) Patent No.: US PP18,378 P2
(45) Date of Patent: Jan. 1, 2008

(54) ***HEMIGRAPHIS* PLANT NAMED 'ATN IM 5'**

(50) Latin Name: *Hemigraphis alternata*
Varietal Denomination: ATN IM 5

(76) Inventor: Lucilene Anatriello, Rua Carmelino Goncalves Condessa 320, 15020020 SP Sao Jose do Rio Preto (BR)

( * ) Notice: Subject to any disclaimer, the term of this patent is extended or adjusted under 35 U.S.C. 154(b) by 0 days.

(21) Appl. No.: 11/396,071

(22) Filed: Mar. 30, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette Para

(57) ABSTRACT

A new and distinct *Hemigraphis* plant cultivar is disclosed, characterized by dark purple/silver black leaves, a flat growth pattern, resistance to dropping older leaves and continuous new shoots from crown of the plant.

1 Drawing Sheet

Latin name of the genus and species: *Hemigraphis alternata.*
Variety denomination: 'ATN IM 5'.

BACKGROUND OF THE INVENTION

The new cultivar 'ATN IM 5' was discovered as a naturally occurring whole plant mutation. The new cultivar was discovered by the inventor in October of 2004 in a cultivated area of São José do Rio Preto, Brazil. 'ATN IM 5' was discovered as a single plant in a field of more than 1000 motherstock plants of the parent variety *Hemigraphis alternata* 'Original Moonlight' (not patented).

Asexual reproduction of the new cultivar 'ATN IM 5' by terminal cuttings and tissue culture was performed in São José do Rio Preto, Brazil and Oxnard, Calif., and has shown that the unique features of this new cultivar are stable and reproduced true to type on successive generations.

SUMMARY OF THE INVENTION

The cultivar 'ATN IM 5' has not been observed under all possible environment conditions. The phenotype may vary somewhat with variations in environment such as temperature, daylength, and light intensity, without, however, any variance in genotype.

The following traits have been repeatedly observed and are determined to be the unique characteristics of 'ATN IM 5.' These characteristics in combination distinguish 'ATN IM 5' as a new and distinct *Hemigraphis* cultivar.

1. Dark purple black leaves with silver tones;
2. Very low mounding, mostly prostrate growth pattern;
3. Resistance to droppping older leaves and;
4. Continuous new shoots from crown of the plant.

Plants of the new cultivar 'ATN IM 5' are similar to plants of the parent variety, in most horticultural characteristics, however plants of the new cultivar 'ATN IM 5' Differ in the following characteristics:

1. More silver tones in the foliage.
2. Greater production of new growth from the crown of the plant.
3. Greater resistance to dropping older leaves 4. Shorter internode length.
5. Shorter overall plant height.

There is not commercial variety to compare to 'ATN IM 5.'

BRIEF DESCRIPTION OF THE PHOTOGRAPH

The accompanying photograph illustrates in full color a typical plant of 'ATN IM 5' grown in a 1 gallon container. One cutting was used in the pot, planted mid May and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'ATN IM 5' plants grown in Oxnard, Ventura County, Calif., during the months of May through October. The growing temperature ranged from 12° C. to 15° C. at night to 12° C. to 20° C. during the day. Measurements and numerical values represent averages of typical flowering types.

Botanical classification: *Hemigraphis alternata* cultivar 'ATN IM 5.'
Commercial classification: Annual foliage plant.

PROPAGATION

Time to rooting: 7 to 14 days at approximately 21° C.
Root description: Very fibrous.

PLANT

Growth habit: Spreading herbaceous annual or tender perennial.
Height: Approximately 14 cm.
Plant spread: Approximately 43 cm.
Growth rate: Fast.
Branching characteristics: Free-branching.
Length of lateral branches: Approximately 13 cm.
Number of leaves per lateral branch: Approximately 16.
Age of plant described: Approximately 146 days.

FOLIAGE

Leaf:
*Arrangement.*—Whorled.
*Average length.*—Approximately 7 cm.
*Average width.*—Approximately 3.5 cm.
*Shape of blade.*—Ovate.
*Apex.*—Broadly acute.
*Base.*—Rounded.
*Attachment.*—Stalked.
*Margin.*—Repand.
*Texture of top surface.*—Very lightly pubescent.
*Texture of bottom surface.*—Lightly pubescent.
*Leaf internode length.*—Approximately 4 cm.
*Color.*—Young foliage upper side: Near Green 139A. Young foliage under side: Near Purple 79A. Mature foliage upper side: Near Green 136A. Mature foliage under side: Near Purple 79A.
*Venation.*—Type: Netted. Venation color upper side: Near Purple 79A. Venation color under side: Near Purple 79A.

Petiole:
*Average length.*—Approximately 3 cm.
*Color.*—Near Purple 79A.
*Diameter.*—Approximately 0.02 cm.

FLOWER

Flowering habit: Sporadic.
Flower form: Raceme.
Natural flowering season. Late spring to late summer.
Number of flowers per lateral branch: Approximately 1.
Flower longevity on plant: Approximately 7 days.
Persistence: Not persistent.

Bud:
*Bud shape.*—Spherical.
*Bud length.*—Approximately 0.3 cm.
*Bud diameter.*—Approximately 0.3 cm.
*Bud color.*—Near White 155B.

Flower:
*Shape.*—Bell-shape, with five fused petals.
*Facing direction.*—Upright.
*Type.*—Simple.
*Aspect.*—Concave.
*Diameter of entire flower.*—Approximately 0.7 cm.
*Length of flower.*—Approximately 0.7 cm.

Petals:
*Appearance.*—Matte.
*Texture.*—Smooth.
*Length of petal.*—Approximately 0.7 cm.
*Width of petal.*—Approximately 0.4 cm.
*Apex shape of petal.*—Acuminate.
*Petal margin.*—Entire.

Color:
*Upper surface at first opening.*—Near White 155B.
*Upper surface at maturity.*—Near Yellow-White 158A.
*Upper surface at fading.*—Near Grey-Yellow 161b.
*Under surface at first opening.*—Near White 155B.
*Under surface at maturity.*—Near Yellow-White 158B.

Fragrance: None.

SEPAL

Number: 5, fused at the base.
Sepal length: Approximately 0.8 cm.
Sepal width: Approximately 0.1 cm.
Apex shape: Narrowly acuminate.
Margin: Entire.
Color: Near Grey-Purple 187A.

Peduncle:
*Length.*—Approximately 4 cm.
*Angle in stem.*—Acute.
*Strength.*—Moderate.
*Color.*—Near Grey-Purple 187A.
*Habit.*—Upright.
*Diameter.*—Approximately 0.1 cm.

REPRODUCTIVE ORGANS

Number of pistils per flower: 1.
Stigma Shape: Needle-shaped.
Stigma Color: Near Red-Purple 72A.
Style Color: Near Red-Purple 69D.
Style Length: Approximately 0.6 cm.
Stamens: 4.
Anther shape: Globular.
Anther color: Near Purple 79A.
Pollen color: No pollen detected.

OTHER CHARACTERISTICS

Disease resistance: Neither resistance nor susceptibility to diseases or pests has been observed in this variety.

Drought tolerance/cold tolerance: Plants are hardy to low temperatures about −2° C. With adequate water plants are hardy to a high temperature of 45° C. Plants do not tolerate drought.

Fruit/seed production: Commercially, this plant is not used or observed in a stage where seeds would be produced. Therefore, seed production has not been observed.

What is claimed is:

1. A new and distinct cultivar of *Hemigraphis* plant named 'ATN IM 5' as herein illustrated and described.

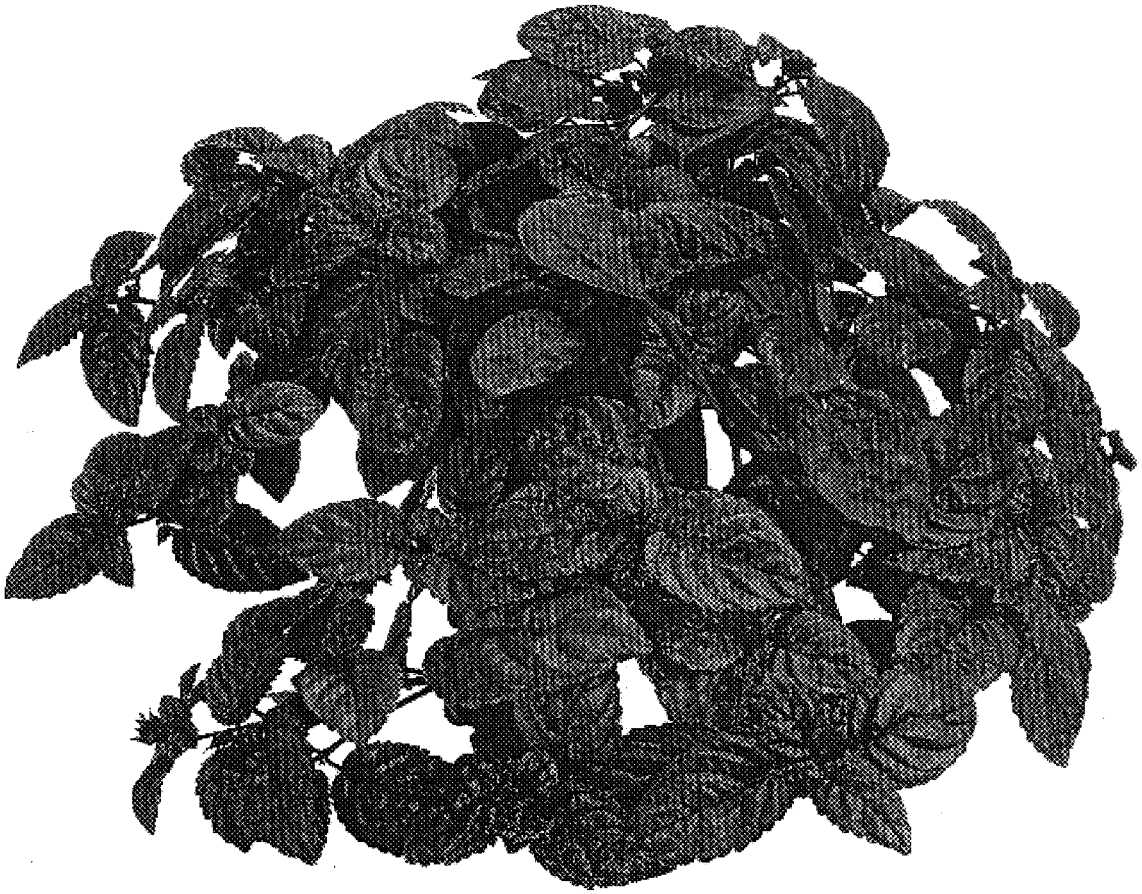

* * * * *